United States Patent [19]

Broadbent, Jr. et al.

[11] Patent Number: 4,555,798
[45] Date of Patent: Nov. 26, 1985

[54] AUTOMATIC SYSTEM AND METHOD FOR INSPECTING HOLE QUALITY

[75] Inventors: William H. Broadbent, Jr., Sunnyvale; Steve Buchholz, San Jose; Peter Eldredge, Santa Clara; Mark J. Wihl, San Jose, all of Calif.

[73] Assignee: KLA Instruments Corporation, Santa Clara, Calif.

[21] Appl. No.: 505,848

[22] Filed: Jun. 20, 1983

[51] Int. Cl.$^4$ ............................................. G06K 9/60
[52] U.S. Cl. .................................... 382/8; 356/237; 358/101; 358/106; 358/107; 382/27
[58] Field of Search .................. 382/8, 22, 27, 28; 358/101, 106, 107; 356/237, 376, 379, 380, 384, 387, 394; 364/560, 563-564

[56] References Cited

U.S. PATENT DOCUMENTS

| | | | |
|---|---|---|---|
| 4,156,231 | 5/1979 | Edamatsu et al. | 382/28 |
| 4,223,387 | 9/1980 | Danielsson et al. | 382/8 |
| 4,319,272 | 3/1982 | Henry | 358/106 |
| 4,379,308 | 4/1983 | Kosmowski et al. | 358/106 |
| 4,417,274 | 11/1983 | Henry | 356/380 |
| 4,500,202 | 2/1985 | Smyth | 382/8 |

Primary Examiner—Leo H. Boudreau
Attorney, Agent, or Firm—Claude A. S. Hamrick

[57] ABSTRACT

An automatic inspection system for inspecting holes in a mask including carriage means 30, illumination means 44, optical means 48, photosensitive detector means 46, and signal processing means 56. The mask 34 to be inspected is positioned by the carriage means in a horizontal plane. The optical means projects a focused image of a portion of the mask onto the photosensitive detector means. Photodiodes in the detector means are responsive to light from the illumination means that is transmitted through the holes in the mask. The signal processing means scans the outputs of the photodiodes and stores in memory a digital representation of the mask. The signal processing means performs inspection measurements and comparison tests. A smoothness checker circuit 240 measures the local radius of curvature of each hole at several places and compares the measurements to predetermined curvature limits to detect nicks and sharp protrusion defects. An area check circuit 246 measures the area of the hole and compares it to predetermined area limits. A diameter check circuit 244 measures the diameter of the hole in two dimensions and compares it to predetermined diameter limits. If either the hole area or the hole diameter is outside their respective limits, a hole size defect is indicated. Means are also provided for locating completely blocked, mispositioned or unintended holes by comparing detected information to a data base.

28 Claims, 18 Drawing Figures

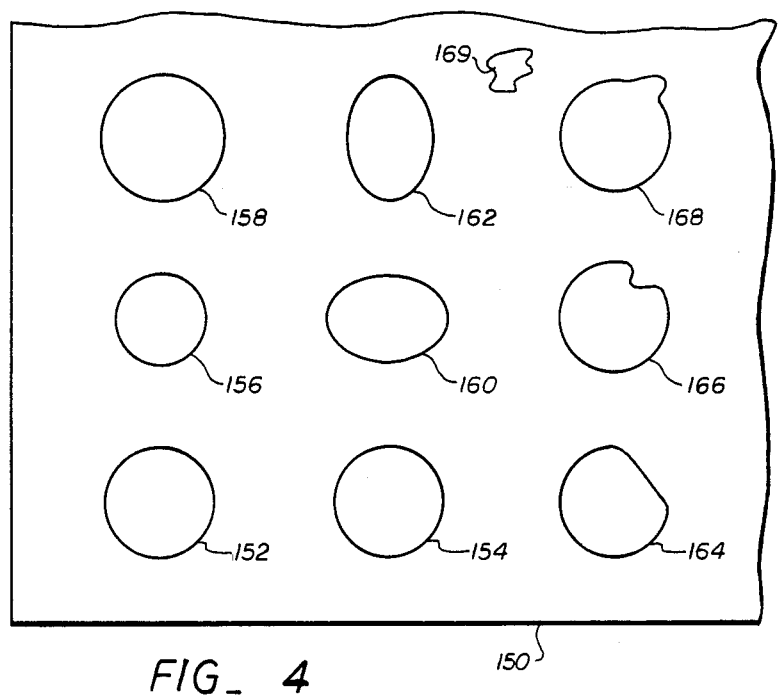
FIG_ 4
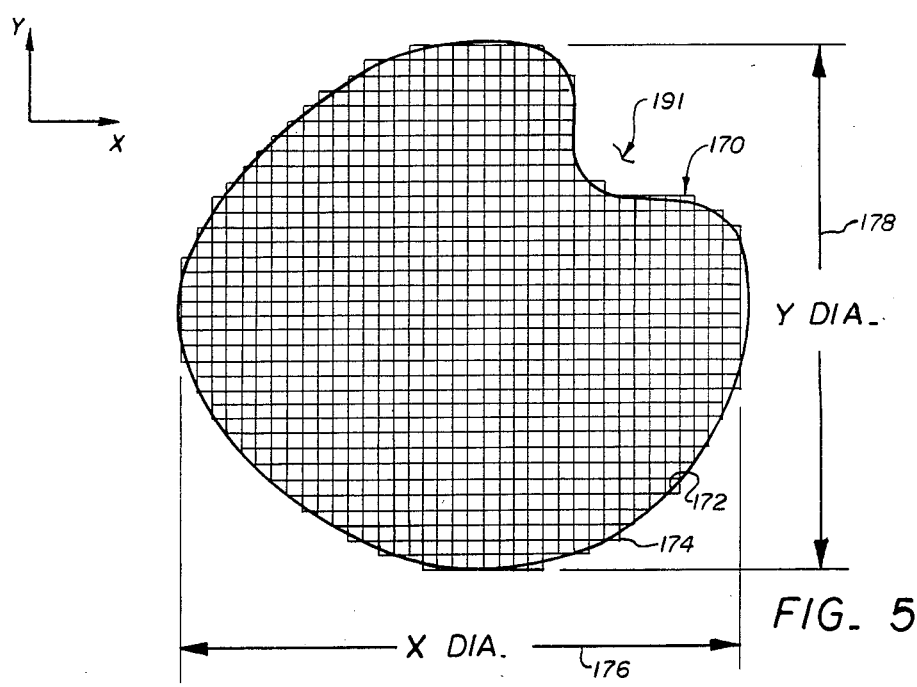
FIG_ 5

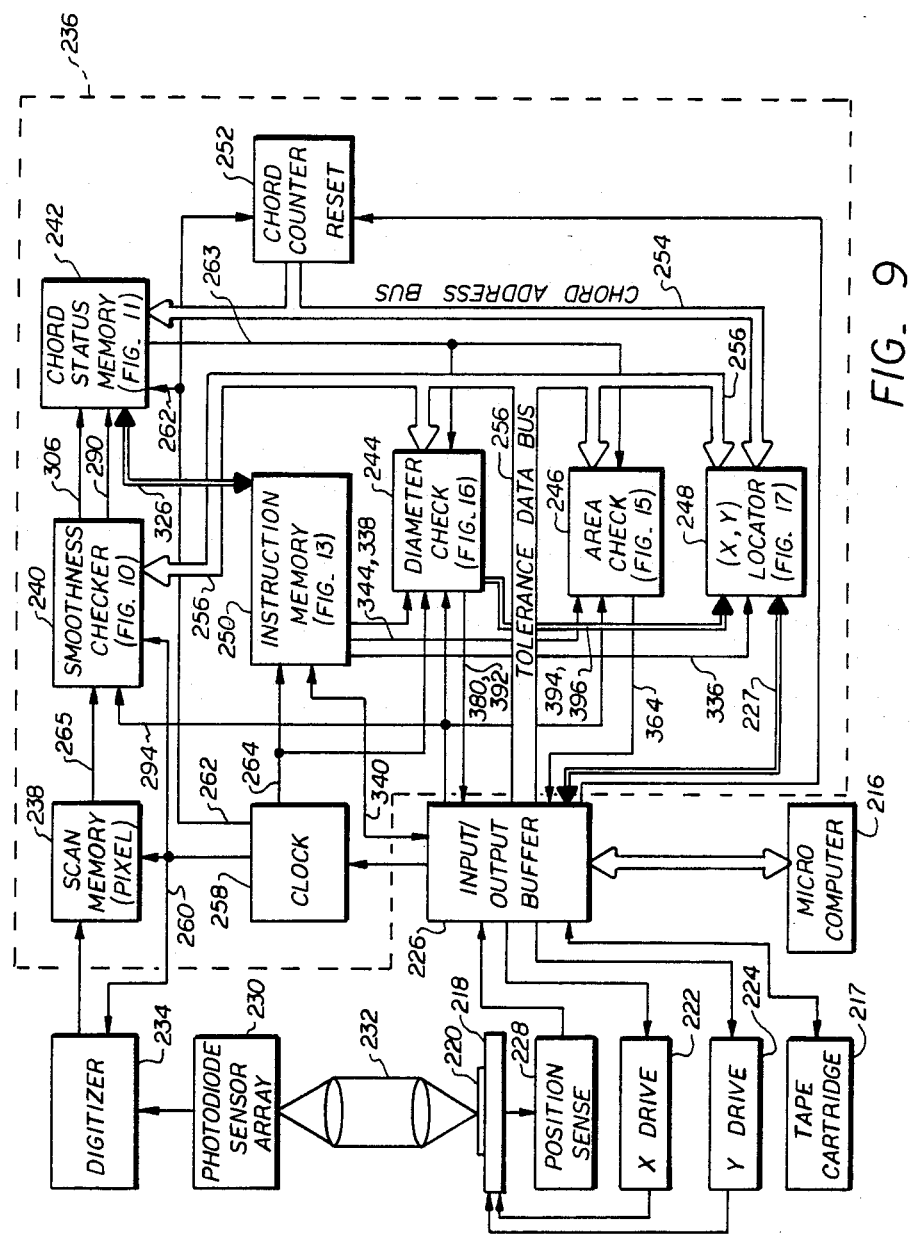

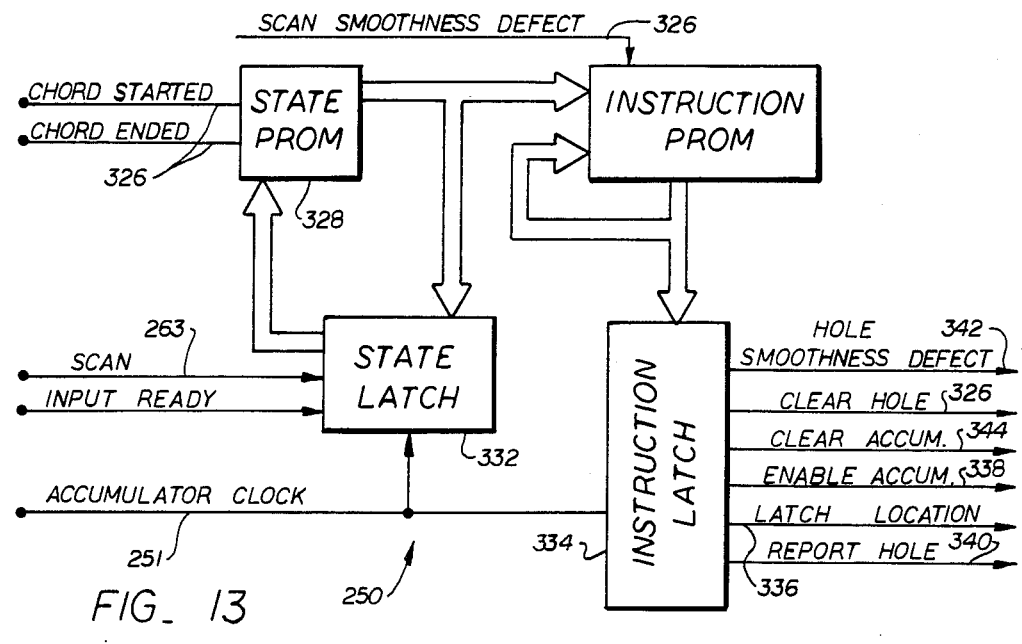
FIG_ 13
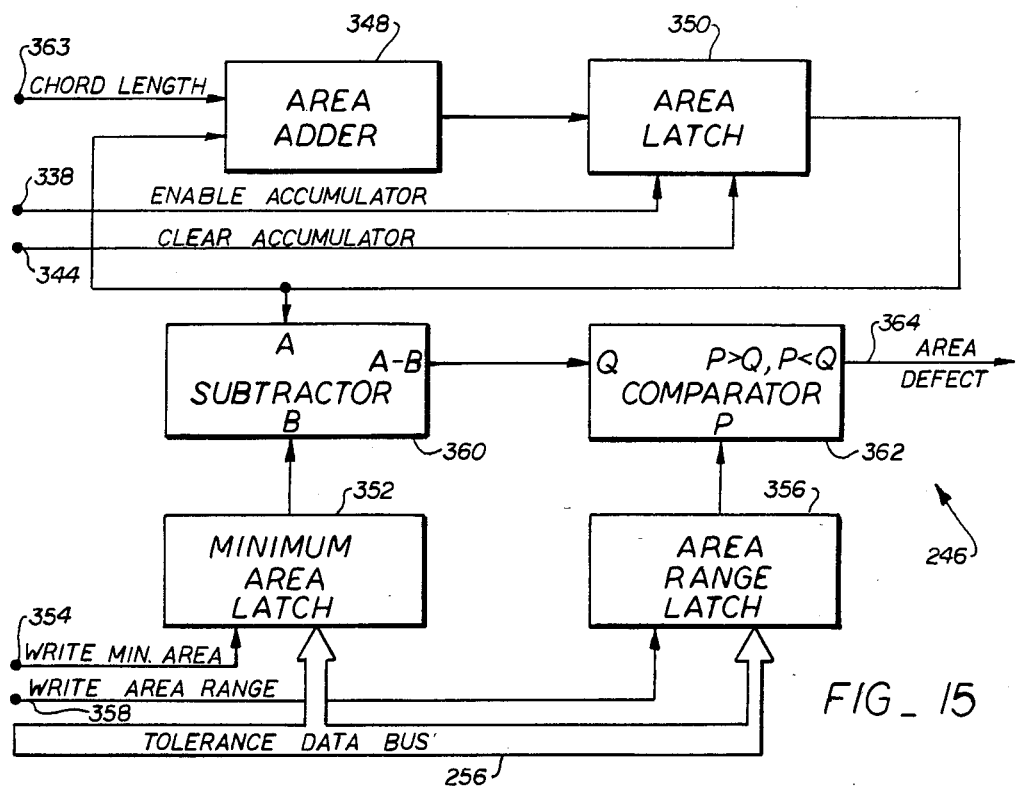
FIG_ 15

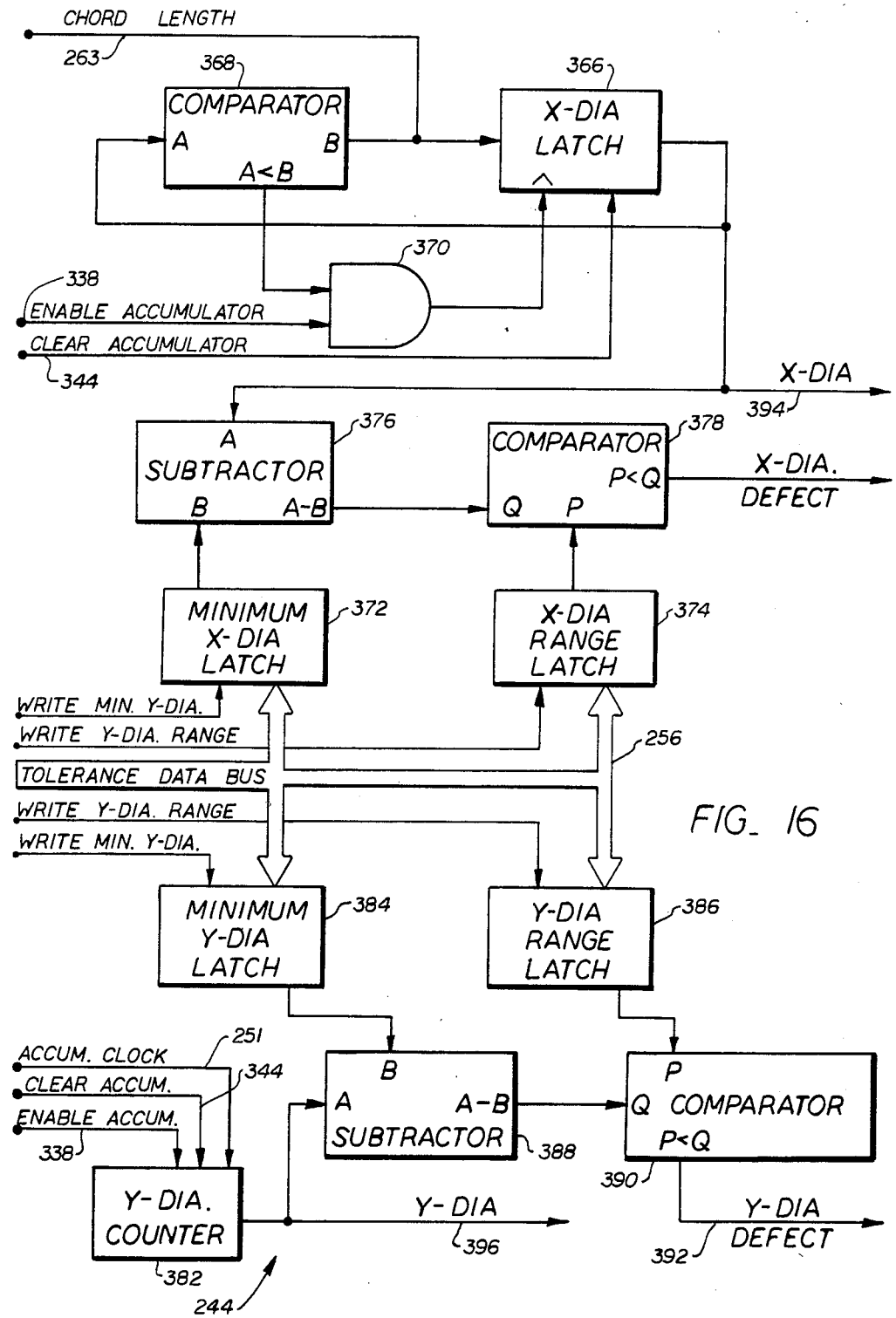
FIG_ 16

AUTOMATIC SYSTEM AND METHOD FOR INSPECTING HOLE QUALITY

BACKGROUND OF THE INVENTION

1. Field of the Invention

This invention relates generally to automatic aperture inspection systems and more particularly to a system and method for automatically inspecting holes in a planar object for defects in size and boundary surfact smoothness.

2. Description of the Prior Art

Metal deposition masks are used by the electronics industry in the manufacture of large scale integrated circuits (LSI). One packaging technique for integrated circuits involves mounting an integrated circuit chip by bonding raised contact pads on a chip to contact pads which have been formed on a matching substrate using a metal deposition mask. These contact pads must be uniform in size and free from contamination to properly interconnect the circuits of the chip to circuits on the substrate. As the complexity of the substrate circuitry and the density of the chips bonded thereto has increased, the cost penalty associated with improper interconnections has also increased. Careful inspection of the deposition masks is therefore necessary to minimize yield loss caused by improperly formed on mispositioned contact pads.

A metal deposition mask is planar in shape with extremely small holes provided therein at positions corresponding to the positions of the contact pads to be formed on one surface of a substrate. To form the contact pads, the substrate and chip wafer with corresponding masks situated thereupon are placed in a metal deposition chamber. The masks allow evaporated metal to be deposited through the holes therein and onto the substrate and wafer only at those positions defined by the holes. The areas of metal thus deposited on the substrate and wafer through the holes in the masks form the contact pads. Since the hole geometry fully defines the contact pads, the uniformity of the resulting contact pads will be a direct result of the uniformity of the holes.

It is therefore necessary that each mask be carefully inspected after manufacture to insure that all holes are properly formed and are free from contamination. The sheer volume of masks that must be inspected dictates that manual inspection is out of the question.

In order to reuse the mask after it is stripped away from the substrate, the metal remaining on the mask is chemically removed in an acid cleaning process. Care must be exercised during the acid cleaning to prevent either incomplete removal of the material which causes completely or partially blocked holes, or over-etching which enlarges the holes. Care must also be exercised in handling the mask to prevent nicking or gouging the holes or contamination. The mask should be inspected after each acid cleaning to insure that the holes have been properly cleaned and are free from residual metal or contamination, and are within size specifications.

Mask inspection is a difficult task. A typical mask may have thousands of holes to be inspected. Inspection by a human operator takes many hours to complete, is subject to fatigue caused errors and is therefore not economically feasible. Additional difficulty arises since defect criteria are subjective and small defects may go unnoticed. When the inspector is under pressure due to volume and yield requirements, it has been shown that there may be considerable divergence between the results he obtains and an unbiased test on the same mask. Even in unbiased tests, many of the smaller defects may be missed and completely blocked holes may be over looked. The common practice of statistical sampling to determine defect density further decreases the confidence lever in the defect density measurement obtained by a human operator.

In addition to inspecting the form, size and position of each hole in the mask, an ideal inspection technique would also inspect the boundary forming edge of each hole for nicks and partial protrusions of metal or contamination. Furthermore, such inspection technique would have objective criteria for the acceptance or rejection of each hole based upon quantifiable and measureable factors, and would perform the inspection rapidly and consistently identifying all known defects for subsequent rework and repair.

SUMMARY OF THE PRESENT INVENTION

It is therefore a principal object of the present invention to provide a novel and automatic metal deposition mask inspection system utilizing objective criteria for identifying defects.

Another object of the present invention is to provide a metal deposition mask inspection system having an operational speed and precision detection capability sufficient to make 100% inspection both practical and economically feasible.

Still another object of the present invention is to provide a system of the type described having objective test criteria stored on mass storage media to minimize set-up time.

Still another object of the present invention is to provide a system of the type described having means for recording defects and for indicating defective holes as well as missing or mispositioned holes.

A further object of the present invention is to provide a system of the type described which utilizes microcomputer technology so as to minimize the number of operator controls and reduce the involvement of the operator in the operation of the system.

A further object of the present invention is to provide a system of the type described which creates a digital representation of the mask using photosensitive detectors, and which analyzes that representation to find defective holes.

A further object of the present invention is to provide a testing method of the type described which creates and continuously analyzes a digital representation of the mask as the mask is displaced with respect to photosensitive detectors.

A further object of the present invention is to provide a system of the type described which is tolerant of misalignment between the mask and the photosensitive detectors.

A further object of the present invention is to provide a system of the type described which measures hole size, boundary surface smoothness and position, and compares such measurements to predetermined limits to identify defective holes.

A further object of the present invention is to provide a method of inspecting the boundary surface smoothness of a hole by analyzing a digital representation of the hole to measure radius of the curvature at several points around the circumference of the hole.

These and other objects, which will hereinafter become apparent, are accomplished in accordance with the illustrated preferred embodiment of the present invention in an inspection system including carriage means, illumination means, optical inspection means, photosensitive detector means, and signal processing means. The mask to be inspected is positioned by the carriage at a series of locations in a horizontal plane. At each location, the optical means projects a focused image of a portion of the mask onto the photosensitive detector means which includes a row of equally spaced photodiodes that respond to light from the illumination means that is transmitted through the holes. The signal processing means scans the outputs of the photodiodes and stores in memory a digital representation of the image projected onto the photodiodes. The mask is then repositioned to project an image of an adjacent portion thereof onto the photodiodes, and the digital representation of that adjacent portion is stored into an adjacent section of the memory.

As the representations of adjacent portions of the mask are stored in memory, the signal processing means performs inspection measurements and comparison tests. A smoothness checker circuit measures the radius of curvature of each hole and compares the measurements to predetermined curvature limits. If the measured radius of curvature is outside the limits, a sharp protrusion or nick defect is indicated. When the digital representation of a hole is complete, an area check circuit measures the area of the hole and compares it to predetermined area limits. In addition, a diameter check circuit measures the diameter of the hole in two dimensions and compares it to predetermined diameter limits. If either the hole area or the hole diameter is outside their respective limits, a hole size defect is indicated.

A microcomputer in the signal processing means interfaces to the smoothness, area, and diameter checking circuits and to the carriage means. By tracking the movement of the carriage means and the location of the holes as detected by the photodiodes, the microcomputer compiles a coordinate map of hole locations and compares it to a predetermined coordinate map to identify blocked and mislocated holes. After the mask has been completely inspected, information is presented to the operator to identify the defects that were found. In addition, the defective holes may be viewed by the operator through a microscope or on a CRT. The location and nature of each defect is then recorded on magnetic tape for future reference or printed out on a report for future reference.

Among the numerous advantages of the present invention is that it provides a 100% inspection of metal deposition masks to objective criteria of hole size, location and boundary surface smoothness.

Another advantage of the present invention is that it permits the selection and modification of such objective criteria.

Another advantage of the present invention is that it automatically inspects a mask, records the outcome of the inspection, and provides a visual representation of the defective holes for viewing by the operator.

Still another advantage of the present invention is that it provides a method of analyzing a digital representation of a hole to determine radius of curvature, area, and diameter.

These and other objects and advantages of the present invention will no doubt become apparent to those skilled in the art after having read the following detailed description of the preferred embodiment which is illustrated in the several figures of the accompanying drawing.

IN THE DRAWING

FIG. 4 is a plan view illustrating a portion of a metal deposition mask to be inspected by the present invention;

FIG. 5 is a schematic view illustrating a defective hole in the mask of FIG. 4 and depicting a digital representation of the hole;

FIG. 9 is a block diagram illustrating the major functional components of the present invention;

FIG. 13 is a block diagram illustrating the functional components of the instruction control memory unit shown in FIG. 9;

FIG. 15 is a block diagram illustrating the functional components of the area check circuit shown in FIG. 9;

FIG. 16 is a block diagram illustrating the functional components of the diameter check circuit shown in FIG. 9;

DETAILED DESCRIPTION OF THE PREFERRED EMBODIMENT

Figure 1:
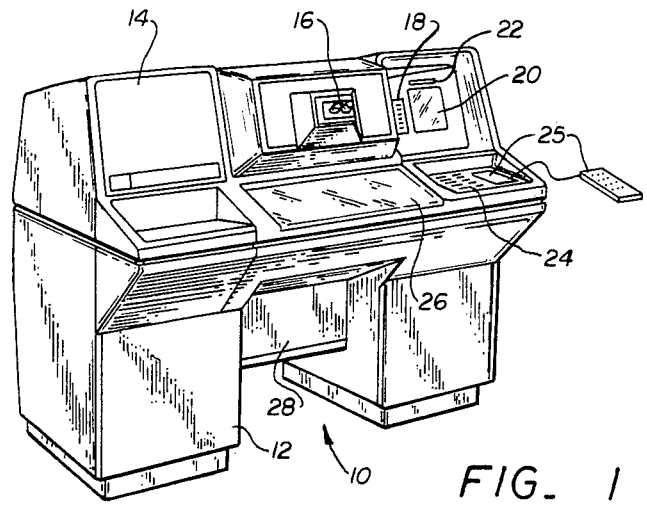
FIG. 1 is a perspective view showing a console that houses the present invention.

Referring now to FIG. 1 of the drawing, a preferred embodiment of the console for housing the present invention is illustrated at 10. In addition to the various processing electronics, this system includes power supplies stored at 12, a roll-out card cage for easy maintenance stored at 14, a binocular head configuration microscope 16, operator controls 18 which are programmed by the system's microcomputer, a cathode ray tube (CRT) display 20 for displaying operator messages and allowing mask viewing, a magnetic tape recorder 22 for storing inspection instructions and a stage and microscope control 24. The system also includes both numeric and alpha numeric keypads as shown at 25. Positioned in and about a mask loading compartment 26 is an air-bearing scanning stage mounted on a granite base, and optical inspection objectives. An illumination system is disposed at 28 beneath the loading compartment 26.

Figure 2:
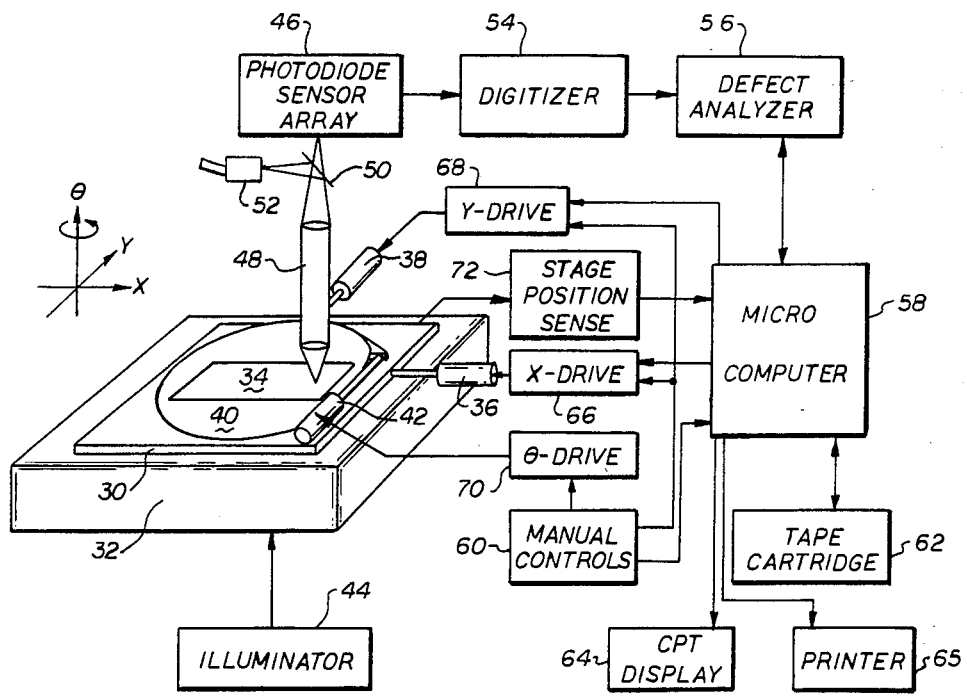
FIG. 2 is a schematic diagram illustrating the functional components of the system used to implement the present invention.

In FIG. 2 of the drawing, the various functional components of the system are schematically illustrated and include an air-bearing stage 30 mounted on a granite table 32 for transporting a mask 34 to be inspected. The stage 30 is movable in the X and Y direction by motors schematically illustrated at 36 and 38, respectively. The mask holder portion 40 of the stage is rotatable in the direction by a motor 42. Disposed beneath the granite table 32 is an illuminator system 44 which illuminates the bottom of mask 34 through an opening in table 32 and which will be described in more detail below.

Light passing through the holes in the mask 34 is focused onto a photodiode sensor aray 46 by an optical system 48. A beam splitter 50 located in the optical path of the optical system 48, focuses a portion of the light onto the binocular head configuration microscope 52. Photodiode sensor array 46 includes a linear array of photodiodes that are equally spaced in a row that is parallel to the Y axis. These photodiodes are responsive to the intensity of light focused thereupon by the optical system 48, and accordingly indicate the relative positions and shapes of the holes in the mask 34. Since the photodiode sensor array is one-dimensional, only a narrow strip of the mask is focused onto the photodiodes at any one time.

A digitizer 54 is coupled to the photodiodes and scans the photodiodes one at a time. The signal output of each photodiode is digitized by comparing each output to a mean reference signal. These signals greater than the mean reference signal are given a value of 1 and those less then the mean reference signal are given a value of 0. Photodiodes corresponding to holes in the mask 34 will have a corresponding value equal to 1. Thus, the narrow strip of the mask focused onto the photodiodes is digitially represented by 1's where holes are located and by 0's between holes.

Since only a narrow strip of the mask 34 is focused onto the photodiode sensor array 46 at any one time, the mask must be repositioned between scans by moving it in the X direction. Each step in the X direction is equal in distance to the resolution between pixels in the Y direction, which in turn is equal to the distance between adjacent photodiodes divided by the magnification of the optical system 48, thus forming square pixels. The length of the narrow strip and, therefore, the width of the swath is a function of the resolution and the number of photodiodes in the array. If that length is less than the width of the mask in the Y direction, the mask must be repositioned in the Y direction after each swath until the entire surface of the mask has been brought into view of the photodiodes. The resulting digital representation of the mask is composed of square pixels with the digital value of each pixel indicating the presence or absence of light.

The digitized signals created by the digitizer 54 as a representation of the mask 34 are transmitted to a defect analyzer 56 for storage in a memory device and analyzed for hole defects, as will later be described in detail. Defect analyzer 56 analyzes each hole in the digital representation of the mask for defects in edge smoothness, area, and diameter according to criteria conveyed to it from a microcomputer 58. Inspection parameters including the hole analysis criteria are input into the microcomputer 58 either manually through manual controls 60 or automatically through a tape cartridge drive 62. Inspection results are communicated to the operator through the CRT display 64 and printed hard copy via printer 65.

Positioning of the mask 34 is controlled by the microcomputer 58 or manual controller 60 through X, Y, and 0 drive system 66, 68, and 70, respectively. The X drive 66 and the Y drive 68, and control motors 36 and 38, respectively, to position the air-bearing stage 30 on the granite block 32. The 0 drive system 70 and motor 42 rotate the mask 34 in the plane of the top surface of the granite block 32. Microcomputer 58 issues positioning instructions to drives 66 and 68, and monitors the resulting stage position through a stage position sense unit 72.

Figure 3:
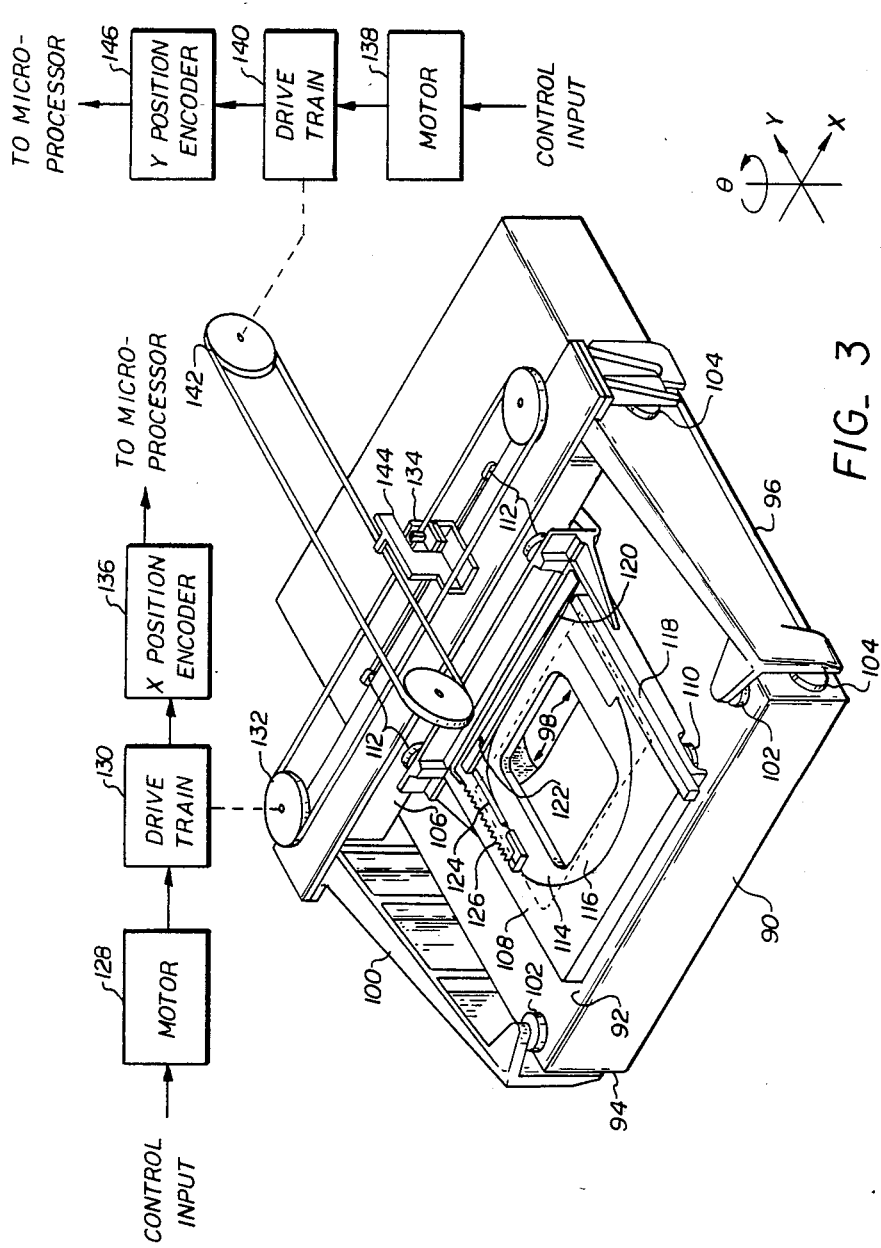
FIG. 3 is a combination block and perspective diagram illustrating a carriage assembly used in accordance with the present invention.

Referring now to FIG. 3 of the drawing, the operative mechanisms forming the air-bearing stage assembly are illustrated, including a granite table 90 which has an extremely smooth and flat top surface 92 and two side surfaces 94 and 96 that are flat and substantially parallel to each other. The granite table also has a hole 98 provided in a central portion thereof through which a mask may be illuminated. A carriage 100 rides across the top 92 on a front and rear pair (not shown) of air-bearings 102 and is constrained to move parallel to surface 96 by air-bearings 104 on the right side and a similar pair of air-bearings (not shown) on the left side. Whereas to the right side, bearings are rigidly affixed to the carriage 100, the left side bearings are spring loaded against the table edge 94 so as to provide a biasing force on the carriage to insure that, while moving, it is guided by the plane of surface 96 which lies parallel to and defines the Y axis.

The carriage 100 also includes a granite cross piece 106 having smooth parallel front and rear sides which extend orthogonally relative to the table surface 96 and therefore lie parallel to and define an X axis. The mask-carrying stage 108 rides across the table top 92 on four corner positioned air-bearings 110, only one of which is shown, and is constrained to move parallel to one of the faces of cross piece 106 by front and rear air-bearings 112. Rotatably mounted to the stage 108 in an aperture plate 114 which supports a mask to be tested. The mask position is illustrated by the dashed lines 116.

Rotation of the aperture plate 114 in the counter-clockwise direction is achieved by energizing a motor located at 118 which, through a lever 120 pivoted at 122, actuates a push rod 124, the distal end of which engages one side of plate 114. A return spring 126 causes clockwise rotation when the drive of motor 118 is reversed.

Movement of the stage 108 in the X direction is accomplished by means of a motor 128 which through a speed-reducing drive train 130 drives a belt-and-pulley mechanism 132, the belt of which is coupled to stage 108 by a bracket 134. Location of the stage 108 in the X direction is monitored by an X position encoder 136 which is coupled to drive train 130 and which generates an output that is coupled into the system microcomputer 58.

Stage 108 is driven in the Y direction by means of a motor 138 which through a speed-reducing drive train 140, a belt-and-pulley mechanism 142, and associated bracket 144 is operatively coupled to the carriage 100. The position of the stage 108 along the Y axis is monitored by a Y position encoder 146 that is coupled to drive train 140 and generates a position signal for input to the system microcomputer.

Since the stage rides entirely on air-bearings, sticking friction is absent and very small movements are possible. The table is also simpler to construct and manufacture than is a conventional machined table with rolling bearings where tight tolerances are required.

In reference now to FIG. 4, a portion of a metal deposition mask 150 is shown that includes several types of defective holes. It is desireable to identify all holes in mask 150 that are larger or smaller than acceptable holes 152 and 154, or that have nicks or protrusions. Defective holes may be round but too small, as is hole 156, or round but too large, as is hole 158. Holes 160 and 162 are not defective because of hole area, but rather are defective due to their oval shapes. Protrusions into holes 164 and 166 cause those holes to be defective, while hole 168 is defective due to a nick. Another type of defect is an extra hole such as that shown at 169. One defect that is not illustrated occurs when the hole is completely blocked.

To selectively identify the defective holes in mask 150, three objective tests are performed. First, the perimeter of the hole must be smooth, or in other words, must have a uniform radius of curvature. Defective holes, such as holes 166 and 168, with sharp protrusions and nicks are identified by this first objective test. Second, the area of the hole must be within certain predetermined limits. This second objective test would identify holes 156 and 164 as too small and hole 158 as too large. Third, the diameter, of the hole as measured in both the X and Y coordinate directions must be within certain predetermined limits. This third objective test would identify hole 160 as defective due to an oversized X diameter, and hole 162 as defective due to an oversized Y diameter. The tolerance range established by the predetermined limits can be tightened or loosened as required. Some defective holes may be identified by more than one of the objective tests. Blocked holes are identified by comparing a coordinate map of holes as detected by the photodiode sensor array 46 to a predetermined coordinate map of holes as they should appear. Holes missing from the detected map are presumed to be blocked. As will be further described below, extra holes are detected by being formed to reside outside of the tolerance area permitted for intended holes.

FIG. 5 illustrates a digital representation 170 of a defective hole 172. Each pixel 174 within the hole 172 has a digital value of 1, as determined by the sensor digitizer and scanner 54. All pixels outside of the hole (not shown) have the digital value of 0. The dimensions of the pixels are determined in the Y coordinate by the spacing of the photodiodes divided by the magnification of the optical system 48 and in the X coordinate by the distance the mask 34 moves between each scan. Accordingly, the pixels may be square or rectangular. The photodiode sensor array 46 may be scanned while the mask is stationary or, alternatively, while the stage 30 and the mask are moving at a constant velocity in the X direction. The velocity selected produces square pixels. Pixels clearly inside or outside of the hole present no problem in determination. Pixels on the perimeter of the hole, however, are slightly more difficult. When the output signal from a photodiode sensing an area on the perimeter of a hole is greater than the mean reference signal, then the corresponding pixel has a value of 1 and that pixel is within the boundary of the hole. In this manner, the pixels approximate the curved perimeter of the hole.

It is preferable, though not required, in this embodiment that the nominal diameter of the hole to be between twenty and fifty pixels in equivalent length. If the pixel size is much greater than one twentieth of the hole diameter, the hole perimeter will be inaccurately represented by a very ragged boundary. If the pixel size is less than one fiftieth of the hole diameter, computation time will increase in the defect detection accuracy.

Once the digital representation 170 of the hole 172 is formed, the three objective tests are performed. The first objective test, that of hole perimeter smoothness, will be described below. The second objective test, that of area checking, is accomplished by counting the number of pixels within the hole and comparing that number to predetermined maximum and minimum limits. If, for example, the nominal hole diameter is thirty-five pixels, then the nominal area will be 962 pixels. In this example, the area limits might be 900 and 1020 pixels, allowing a 120 pixel tolerance range. The third objective test involves checking the X and Y hole diameters 176 and 178, which are found by counting the number of pixels that span the hole in X and Y. If, for example, the nominal hole diameter is thirty-five pixels, the acceptable limits may be thirty-three and thirty-seven, allowing a four pixel tolerance range. Tighter or looser tolerances than the example given may be utilized as required.

Figure 6:
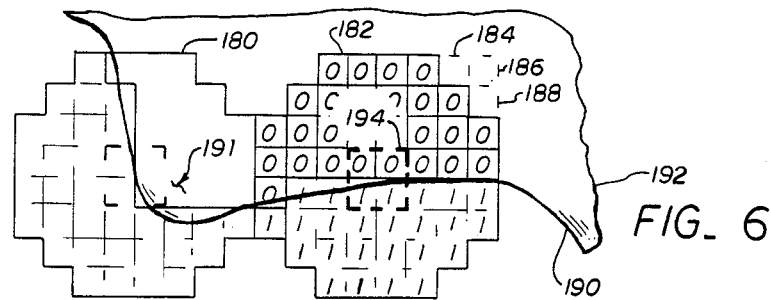
FIG. 6 shows a portion of the defective hole of FIG. 5 illustrating the detection of a smoothness defect.

In reference now to FIG. 6, the operation of the first objective test will be described. The goal of this test is to detect nicks and protrusions by examining the radius of curvature of the digitized hole boundary. The background theory is as follows: Define a circle having a diameter substantially smaller than that of the hole. Position the circle such that its center is on the boundary of the hole. If the boundary is smooth at that point, the overlap area will be slightly less than one half of the total circle area. If the center of the circle is on the hole boundary at a position having a small radius of curvature, which is indicative of a nick or sharp protrusion, the overlap area will be substantially less than or greater than one half of the total circle area.

According to the present invention, the aforementioned circle is approximated by the clusters of fifty-two pixels shown at 180 and 182. Clusters 180 and 182 are squares of eight-by-eight pixels with three pixels 184, 186 and 188 removed from each corner. The resulting fifty-two pixel clusters 180 and 182 are positioned at the boundary of a hole 190 in the mask 192. Hole 190 has a protrusion defect 191 similar to that of hole 172 (FIG. 5). Positioning the cluster 182 on the boundary of hole 190 is accomplished by monitoring the values of the four center pixels 194. When two of the four center pixels have values of 1 and the other two have values of 0, the cluster is properly positioned. To measure the overlap area, the number of pixels (digital 1's) within the hole are counted. In the case of cluster 180, the overlap area is thirty-four pixels, while one half of the cluster area is twenty-six pixels. If, for example, the limits on overlap area are twenty-two and thirty pixels, cluster 180 would indicate a defect. Its overlap area is substantially greater than one half of the total area because the protrusion has a small radius of curvature. In the case of cluster 182, however, the overlap area is twenty-five pixels, which would be within the acceptable limits. Even though the portion of the boundary examined by cluster 182 deviates from the nominal hole boundary, a defect is not indicated by this cluster since the local radius of curvature is large. The defect will be indicated however, by any cluster, such as cluster 180, that is located at the sharply curving portion of the boundary.

Figure 7:
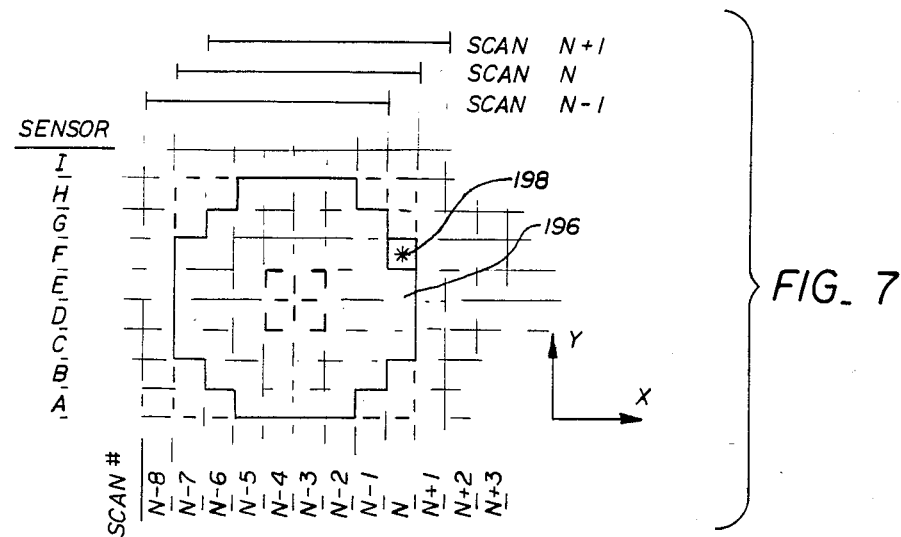
FIG. 7 is a schematic showing of a cluster of pixels as used by the present invention to determine hole defects.

The organization of pixel data comprising the digital representation of the mask is shown in FIG. 7. A cluster 196 includes the pixel data from eight photodiodes A through H, which although not shown, may be considered to move along the depicted rows A through H during eight consecutive scans, N−7 through N. Reviewing for a moment the manner of forming the digital representation, recall that the photodiodes are arranged in a row that is oriented in the Y direction. The photodiode array is scanned one photodiode at a time, from one end of the array to the next. The mask is then repositioned relative to the mask and the photodiode array is scanned again. This process repeats until the entire mask has been covered.

In order to increase inspection throughput and to minimize data storage requirements, the present invention performs inspection calculations as the photodiode array is scanned. The inspection process need not be delayed until a hole is completely digitized. Only the pixel data from the current scan (N) and the seven previous scans (N−1 to N−7) are stored in a pixel memory; such data forming an eight-by-eight pixel cluster. Cluster 196 includes a pixel (N,F) 198, which is the digitized output from photodiode F during scan number N. The photodiodes A through G are the eight most recently scanned photodiodes of scan N, and their outputs are represented in cluster 196 as pixels (N,A) through (N,H). The remainder of cluster 196 consists of pixels corrsponding to the outputs of photodiodes A through H as digitized during scans N−1 through N−7, the seven previous scans. The four center pixels (N−3,D), (N−3,E), (N−4,D), and (N−4,E) are used to determine when cluster 196 is positioned at a hole boundary. After the computation using cluster 196 is completed, photodiode I is scanned and the next adjacent cluster is formed for inspection computations. This adjacent cluster includes pixels located at B through I and N through N−7. After scan N is complete, scan N+1 will begin, and the pixel data from scan N−7 will be dropped from memory as it is no longer needed. Thus, each cluster used sixty-four pixels, some of which are truncated during the inspection computations. Note that each pixel is contained in sixty-four different clusters that are adjacent in space and adjacent in time.

As previously mentioned, the present invention performs the inspection computations on pixel data from the current scan and the seven immediately previous scans. Since the holes to be inspected are larger than eight pixels in diameter, running computations relating to the smoothness, area and diameter measurements must be made. To accomplish this, the defect analyzer 56 (FIG. 2) includes a chord memory (in addition to the pixel memory) that stores the hole inspection information as it is generated. Each pixel in the Y direction, which is equal in number to the number of photodiodes, has a corresponding location in the chord memory.

Figure 8:
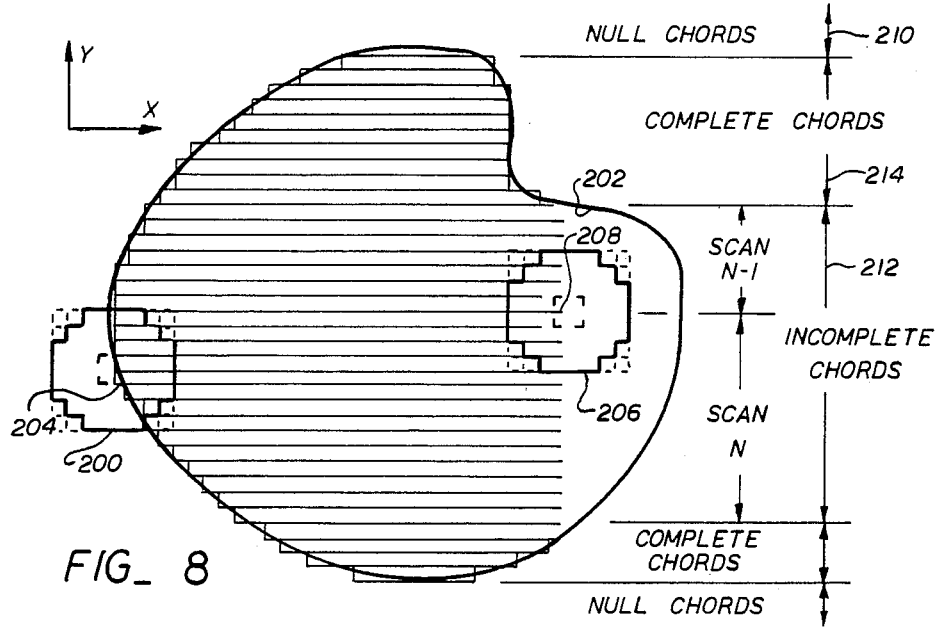
FIG. 8 is a schematic showing of the defective holes of FIG. 5 illustrating the method of measuring area and diameter of holes.

FIG. 8 depicts the relationship between the organization of the chord memory, the pixel memory and the pixel data that represents the hole being inspected. When the inspection of a mask is begun, pixel data is generated starting with the left most edge of the mask. Each pixel along a row parallel to the Y axis is sequentially formed during a scan at a constant X dimension. A margin from the left edge of the mask to the first hole must be at least eight pixels wide to fill an eight pixel wide pixel memory before the first hole is encountered. The pixel memory has eight columns, each corresponding to a scan in Y, and as many rows as there are photodiodes. Once the pixel memory is full, the pixels from the earliest of the eight scans are dropped and the remaining pixels are shifted backward by one column at the end of each scan. During the following scan, the pixels generated during that scan are added one at a time to the first column of the pixel memory. As each pixel is added to the pixel memory, an eight-by-eight cluster of pixels is formed for the inspection computations. This cluster, as described above, includes the eight pixels that were most recently generated during the current scan plus seven pixels in each of the eight corresponding rows.

The chord memory has one 12-bit location assigned to each Y-diode position. The Y-diode number is used as the address to the memory. The 12-bits are used to represent three flags (ie, a start chord, an end chord and a smoothness defect), an 8-bit chord length, and one unused bit position.

As each cluster is formed, its center four pixels are examined to detect a hole boundary. When two of the four pixels have values of 1 and the other two have values of 0, a hole boundary is indicated. In FIG. 8, cluster 200 has detected the boundary of hole 202 since two of its four center pixels are within the hole. When a boundary is detected, the smoothness is checked by counting the number of pixels within the hole as described above. If a smoothness defect is found, the smoothness defect flag bit is set in the location of the chord memory that corresponds to the Y-diode number of pixel 204. In addition, the start chord flag is in the chord memory at that location. After those flags are set, the inspection computation for pixel 204 is complete.

In order to measure the area and diameter of hole 202, the hole is represented by chords, with each chord corresponding to the pixels in one row of the digital representation that spans the hole. Each location or row of the chord memory includes three flags indicating the presence of a smoothness defect, whether the chord has been started, whether the chord has been ended, and a number equal to the length of the chord in pixels. Each time a cluster if located with its center at the hole boundary, smoothness is checked and either the start chord flag or the end chord flag is set, according to whether the cluster is on the left side or the right side of the hole. If the cluster 206 is centered within the hole, the chord length of chord 208 is incremented by one during the inspection calculation.

By updating the chord memory during each inspection calculation, the measurement of the hole is accomplished without the need to store all the pixels in memory. Chords above and below the hole are null chords 210, having neither the start chord flag nor the end chord flag set. When a chord has been started but not ended, it is an incomplete chord 212 and is incremented in length during each scan. When a chord has been both started and ended, it is a complete chord 214. A completely inspected hole is designated by a grouping of completed chords bounded by null chords and without any incomplete chords within the grouping.

One advantage to analyzing the pixel data in the above described manner is that memory requirements are minimized. By establishing the chord memory that corresponds to the photodiode array, several holes can be accumulated simultaneously in a scanning data format. After a hole is first detected, the portion of the chord memory corresponding to the photodiodes detecting that hole is updated with each scan until the hole has been completely covered. Only after the hole is complete are the area and diameter inspection tests performed. However to avoid ambiguity the holes must be spaced on the mask such that detection of all chords of a hole must be completed before any of those chord positions are used to begin accumulating data corresponding to a new hole.

Once all the chords in a hole are complete, the three objective tests are performed. If the smoothness defect flag has been set for any of the chords corresponding to the hole, it is defective. The hole area is found by summing the lengths of all of the completed chords corresponding to that hole, and is compared to its predetermined limits to find oversize and undersize holes. The hole diameter in the X direction is equal to the longest chord length. The hole diameter in the Y direction measured in pixel units is equal to the number of completed chords corresponding to that hole. The diameter values thus calculated are compared to the predetermined diameter. The coordinate location of the center of the hole is determined by calculating one half of the X diameter and one half of the Y diameter. These two dimensions are referenced to the mask coordinates determined by the X-stage position when the hole is reached and the Y-stage position and Y-diode number of the lowermost chord. This measured hole location will then be compared by the microcomputer 589 to a predetermined map to check for blocked holes.

FIGS. 9 through 16 describe the functional details of the electronic circuit, according to the present invention that performs the necessary calculations and control functions. Specifically, FIG. 9 is an overall schematic diagram of the present invention. The microcomputer 216 controls the position of the air-bearing stage 218 and the mask 220 affixed thereto by controlling the X drive unit 222 and the Y drive unit 224 through an input/output buffer 226. Position feedback for the stage 218 is provided to the buffer 226 by the stage position sense unit 228. An image of a portion of mask 220 if focused onto the photodiode sensor array 230 by the optical system 232. The digitizer 234 is operable for assigning a digital value of 1 or 0 to the signal outputs of each of the photodiodes in the photodiode array 230. Hole inspection is carried out by the defect analyzer 236 in response to the photodiode signal digitized by digitizer 234, and is reported to the microcomputer through the input/output buffer 236.

As previously described, the defect analyzer 236 accumulates and analyzes holes as they are detected by the photodetector array 230. A scan memory 238 holds the pixel memory data for the current scan and the seven immediately previous scans. The defect analyzer operates in one of four states, depending upon the location of the currently defined cluster of pixels in relation to the holes. When the cluster is outside the boundaries of the holes, as determined by its four center pixels, the defect analyzer is in the idle state. While in the idle state, the defect analyzer essentially waits until a cluster encounters a hole, whereupon it shifts into the accumulate state. In the accumulate state, the defect analyzer checks for smoothness when a cluster is centered at the boundary, sets the appropriate start and end chord flags, and increments the chord length register. When the defect analyzer is accumulating several different holes during each scan, the state shifts from accumulate to idle when the cluster leaves one hole boundary, then shifts to accumulate again when the next hole is encountered. Whenever a hole is completed, the defect analyzer shifts to the report state and performs the objective tests to identify area and diameter defects. After reporting a hole, the defect analyzer shifts to the reset state and clears that portion of the chord memory that corresponds to the hole just reported. Then it shifts to the idle state and waits for another hole to appear.

The defect analyzer 236 includes several related circuits that perform the hole accumulation and objective testing tasks. A smoothness checker 240 accepts pixel data from the scan memory 238 and forms a cluster therefrom to analyze hole boundary crossings and smoothness. A chord status memory circuit 242 used the four center pixels of the cluster formed by the smoothness checker and update the chord memory according to the position of the cluster in relation to any holes. A diameter check circuit 244 and an area check circuit 246 respectively compute the hole diameters and area from information contained in the chord status memory 242 and compare those values to predetermined limits.

Figure 9A:
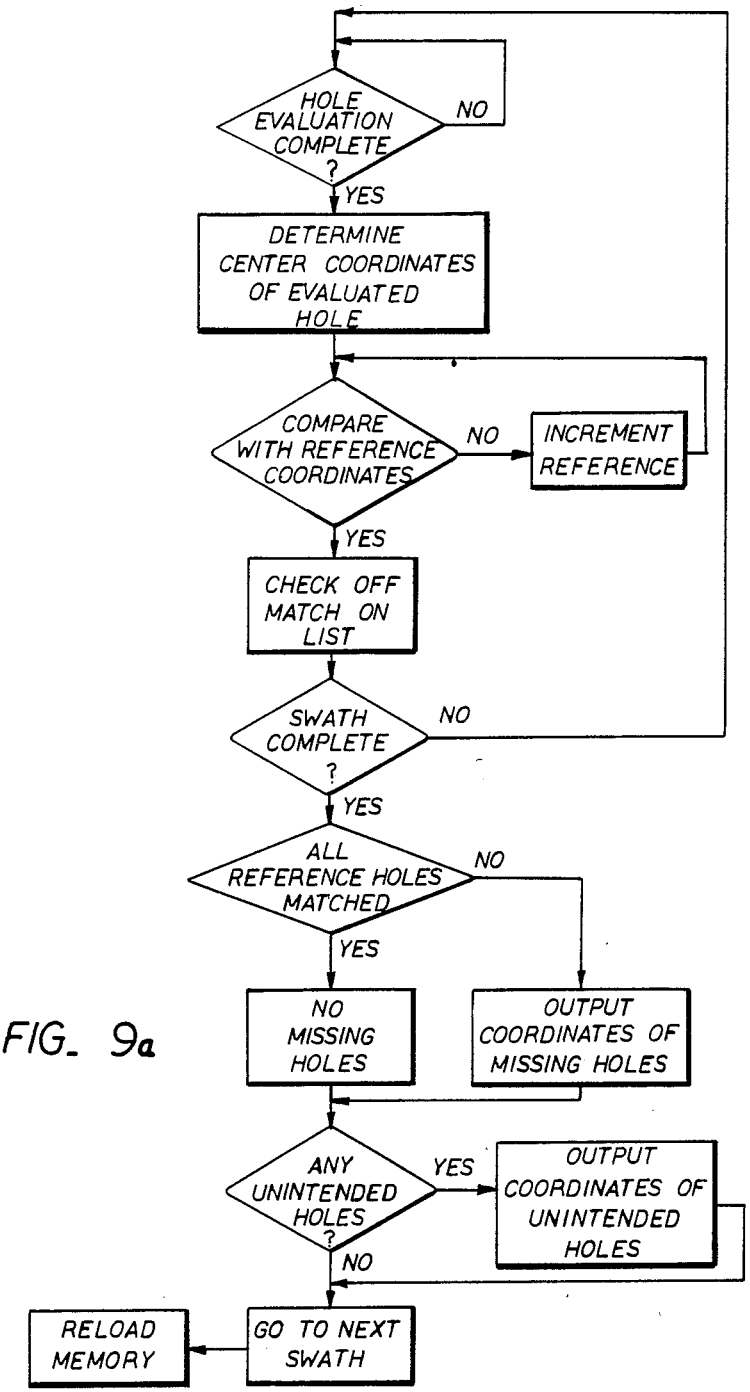
FIG. 9a is a flow diagram illustrating the hole evaluation operation performed in accordance with the present invention.

To find missing holes, (that might actually be completely blocked), or unintended holes, a set of reference coordinates of all intended holes in the present swath across the mask (one Y-scan) is loaded from the tape cartridge 217 into the (X,Y) locator 248 by the microcomputer 216 prior to the swath execution. In addition, a tolerance band is loaded which indicates how far away the intended hole may be from the reference coordinates while still matching the reference coordinate. As the scan passes over a particular hole, the (X,Y) locator 248 computes the aproximate center of the hole from the X and Y chord information. This coordinate is then compared with the reference coordinates to find a reference coordinate which includes the actual coordinate of the hole just encountered within the allowed tolerances. The hole corresponding to that reference coordinate is then considered "found" and is reported to the microcomputer. At the end of the swath, the microcomputer identifies any reference coordinates that were not "found" as missing holes, and any encountered holes which did not match a reference coordinate within the allowed tolerance as on unintended hole. A flow diagram illustrating this operation is shown in FIG. 9a.

An instruction memory circuit 250 controls the transition from state to state according to stored instructions and inputs from the chord status memory and the microcomputer. A chord counter 252 tracks the Y coordinate of the current cluster and relays that information to the chord status memory 242 and the (X,Y) locator 248 via a chord address bus 254. Data defining the limits for use with the objective defect tests are input to the smoothness checker 240, the diameter check circuit 244, and the area check circuit 246 by the microcomputer through the input/output buffer and a tolerance data bus 256.

Timing for the various circuit functions is provided by a clock 258 which provides the following timing signals: a scan clock signal 260 to the sensor digitizer and scanner 234, the scan memory 238, and the smoothness checker 240; a chord clock signal 262 to the chord status memory 242 and a chord counter 252; and an accumulator clock signal 264 to instruction memory 250 and diameter check 244 circuits. The chord clock signal 262 provides a delay relative to the scan clock signal 260. Similarly, the accumulator clock signal 264 provides a delay relative to the chord clock signal 262.

Figure 10:
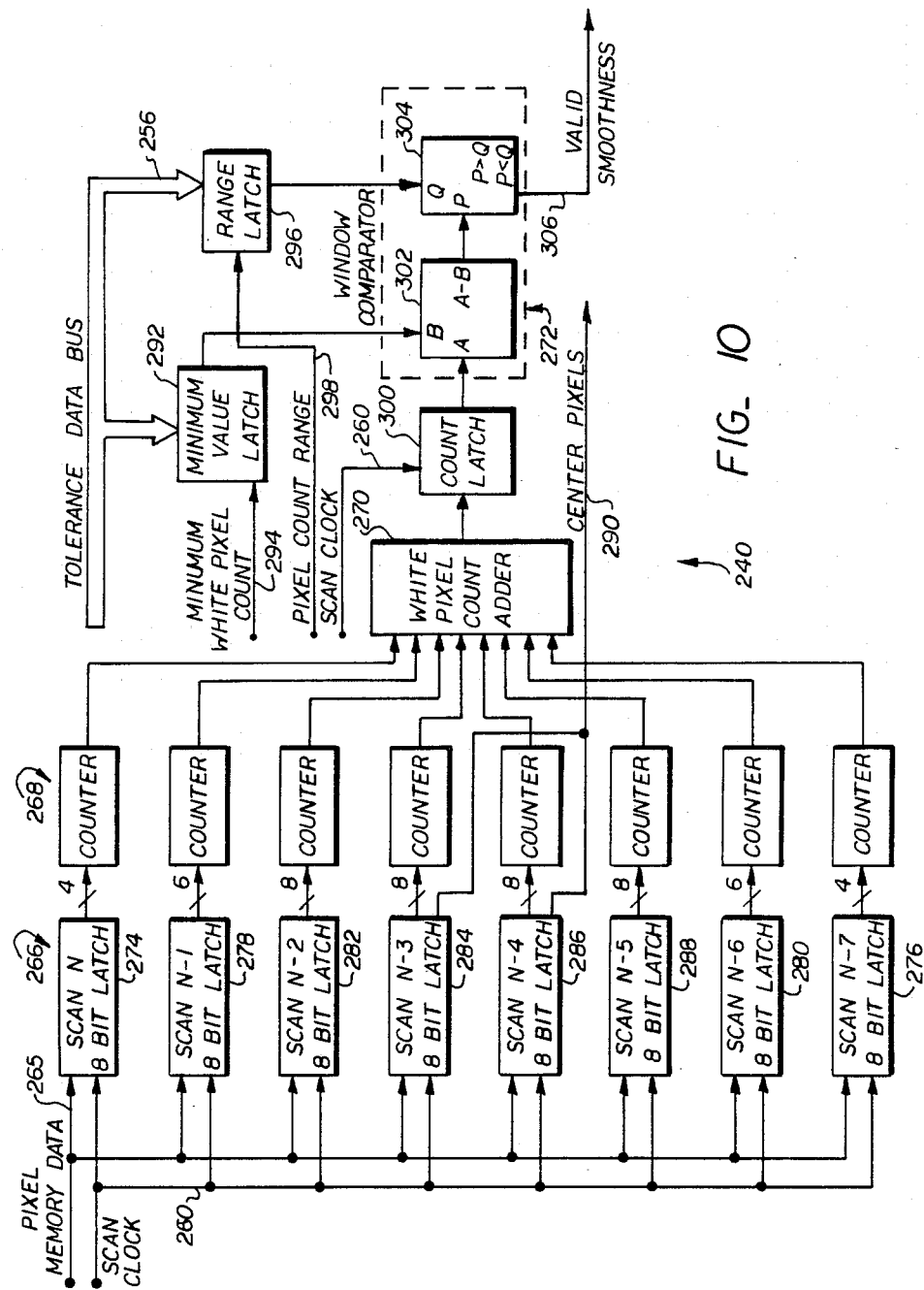
FIG. 10 is a block diagram illustrating the functional components of the smoothness checking circuit shown in FIG. 9.

The smoothness checker circuit 240, shown in detail in FIG. 10, includes eight latches 266, eight counters 268, a count adder 270, and a window comparator circuit 272. Pixel data from the scan memory 238 is clocked into the latch by the scan clock signal 260. Each of the eight latches is eight bits in length and holds the pixel data from one scan of eight photodiodes. Each clock pulse of scan clock 260 drops one bit and loads a new bit into each latch. This in effect moves the cluster defined above by one pixel in the Y direction. In order to approximate a circle, only fifty-two of the sixty-four pixels are counted to inspect hole smoothness. Accordingly, the center four pixels of latches 274 and 276, the center six pixels of latches 278 and 280, and all eight pixels of latches 282, 284, 286, and 288 are counted by the counters 268 and summed by the count adder 270 to determine how may of the fifty-two pixels are within the hole. The values of the four center pixels for the cluster, as stored in latches 284 and 286, are output to the chord status memory 242 via line 290.

To perform the objective test for smoothness, the smoothness checker circuit 240 utilizes the window comparator circuit 272. A minimum acceptable value is clocked into a minimum value latch 292 from the tolerance data bus 256 by a clock pulse on a minimum white pixel count line 294 which originates at the microcomputer 216. Similarly, a range that, when added to the minimum value yields the maximum acceptable value, is clocked into a range latch 296 by a clock pulse on a pixel count range line 298. After the pixels in the cluster are counted by the count adder 270, the next clock pulse on the scan clock line 260 loads that count into a count latch 300. A substractor 302 subtracts the minimum value from the cluster count and inputs the difference to a comparator 304. If this difference is less than the range and greater than zero then comparator 304 outputs a logic high value as a valid smoothness signal 306. If the cluster count is less than the minimum value, or greater than the maximum value, the valid smoothness signal 306 is logic low. This test is performed on every cluster, one per clock pulse, whether or not the cluster is at a hole boundary. Window comparison circuits are also used in the diameter check circuit 244 and the area check circuit 246.

Figure 11:
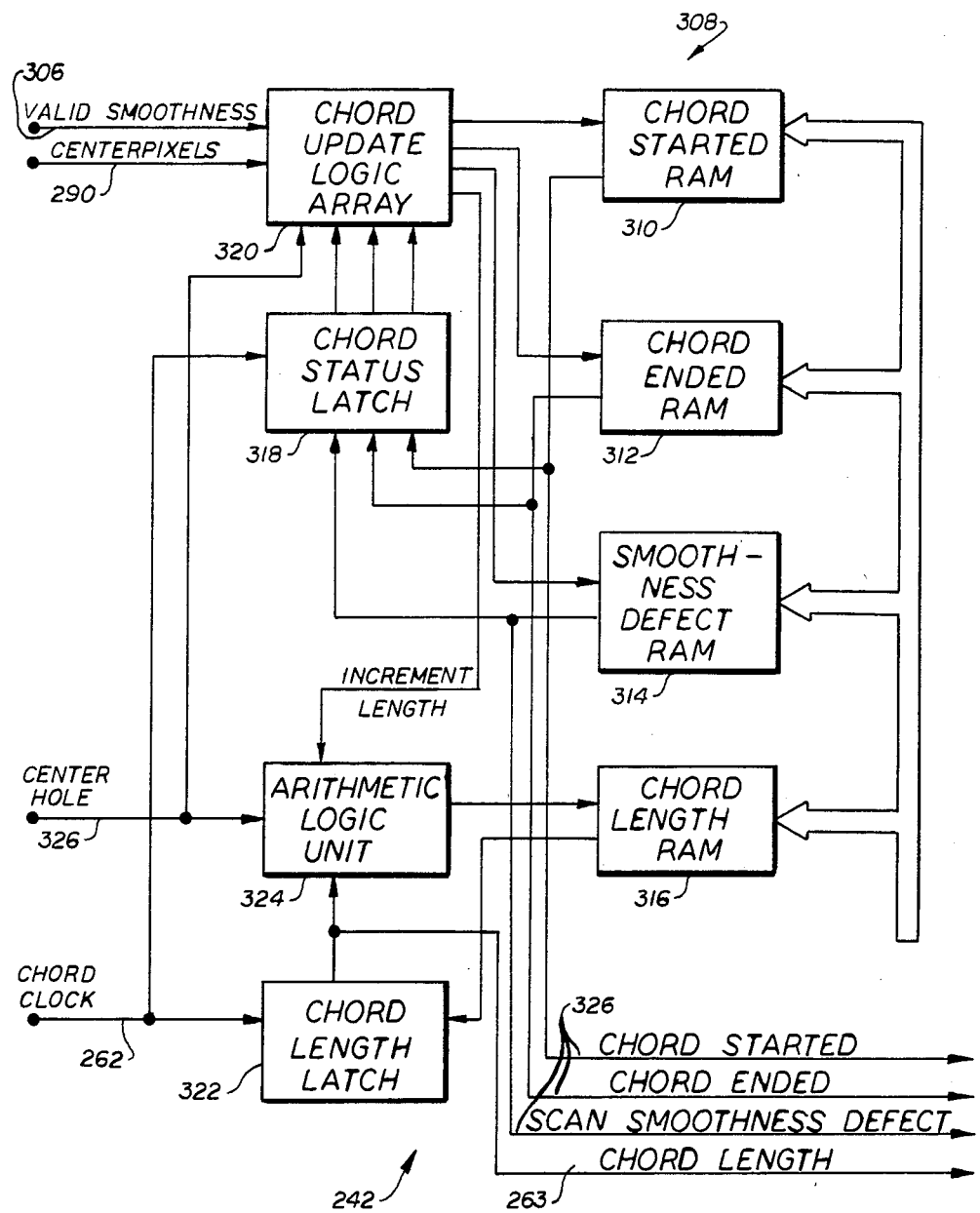
FIG. 11 is a block diagram illustrating the functional components of the chord memory circuit shown in FIG. 9.

Data that is characteristic of the holes being inspected is stored in the chord memory 308 by the chord status memory circuit 242, as shown in FIG. 11. The chord memory 308 consists of four random access memory circuits (RAM) which are: chord started RAM 310, chord ended RAM 312, smoothness defect RAM 314, and chord length RAM 316, each of which has one memory address for each photodiode. The chord started RAM 310, the chord ended RAM 312, and the smoothness defect RAM 314 are one bit long and serve as flags to signify started chords, ended chords, and smoothness defects, respectively. The chord length RAM 316 provides storage for the magnitude of the length of the chords, as measured in pixel units. Memory locations in each of the RAM's is acessed by an address transmitted via the chord address bus. A chord status latch 318 latches the current values of the chord memory in response to the chord clock 262. A chord update logic array 320 monitors the current chord memory values and the valid smoothness and center pixels signals 306 and 290, respectively, from the smoothness checker 240 to determine if and when to update the chord memory. In order to update the chord length RAM 316, a chord length latch 322 and an arithmetic logic unit 324 are provided. A clear hole signal 326 that originates from the instruction memory 250 instructs the chord update logic array 320 to clear portions of the chord memory 308 as required during the reset state.

Figure 12:
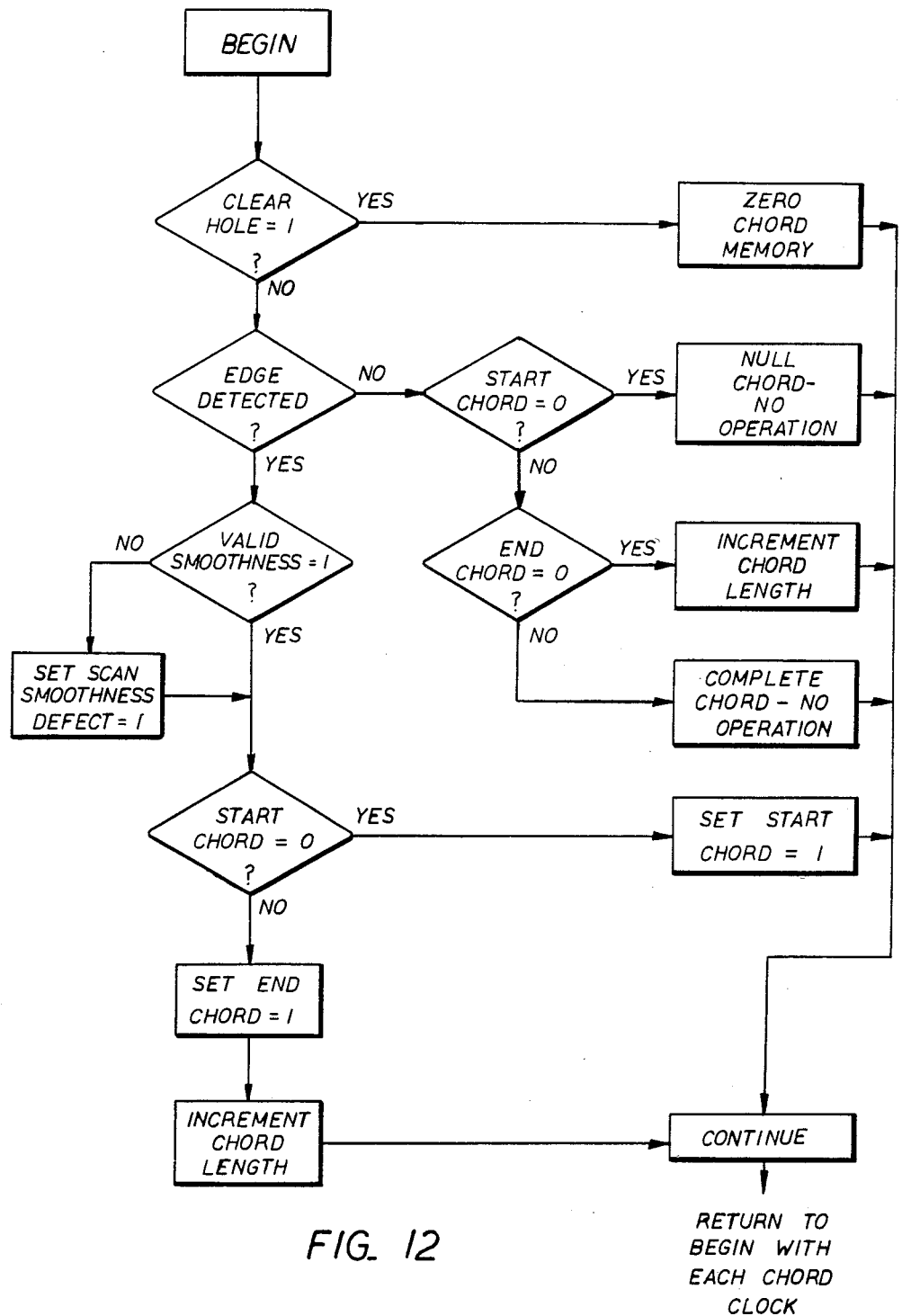
FIG. 12 is a flow diagram illustrating the logical steps used in the operation of the chord memory circuit of FIG. 11.

The logical steps that the chord update logic array 320 follow, shown in FIG. 12, are responsive to the status of the chord memory and the current cluster. The first test performed by logic array 320 is whether the clear hole signal 326 is logic high. If so, then the logic array clears the chord memory 308 at the current chord address. If not, then the four center pixels (lines 290) are examined to determine if the current cluster of pixels is located on a hole boundary. If yes, then the valid smoothness signal is examined for indication of a smoothness defect. If no valid smoothness, then a flag is set at the current chord address in the smoothness defect RAM 314. The next test when the cluster is at a hole boundary is to decide whether to start or to end a chord. If a chord has not yet been started at the current chord address, a flag is set in the chord started RAM 310 and if a chord has already been started, a flag is set in the chord ended RAM 312 and the chord length in the chord length RAM 316 is incremented by one.

When the current cluster is not at a hole boundary, another series of tests are performed. The chord started RAM 310 is examined to determine if the current location of the cluster is on a null chord or a started chord. If the cluster is at a null chord, no operation is required and the logic array 320 waits for the next clock cycle. If the cluster is not at a null chord, it must be at either a complete chord or an incomplete chord. If a flag is set in the chord ended RAM 312, the chord is complete and no operation is required. If the flag is not set, then the chord is incomplete and the chord length RAM 316 is incremented by one. One cycle is now complete, so the logic array waits for the next clock cycle before taking further action.

Figure 14:
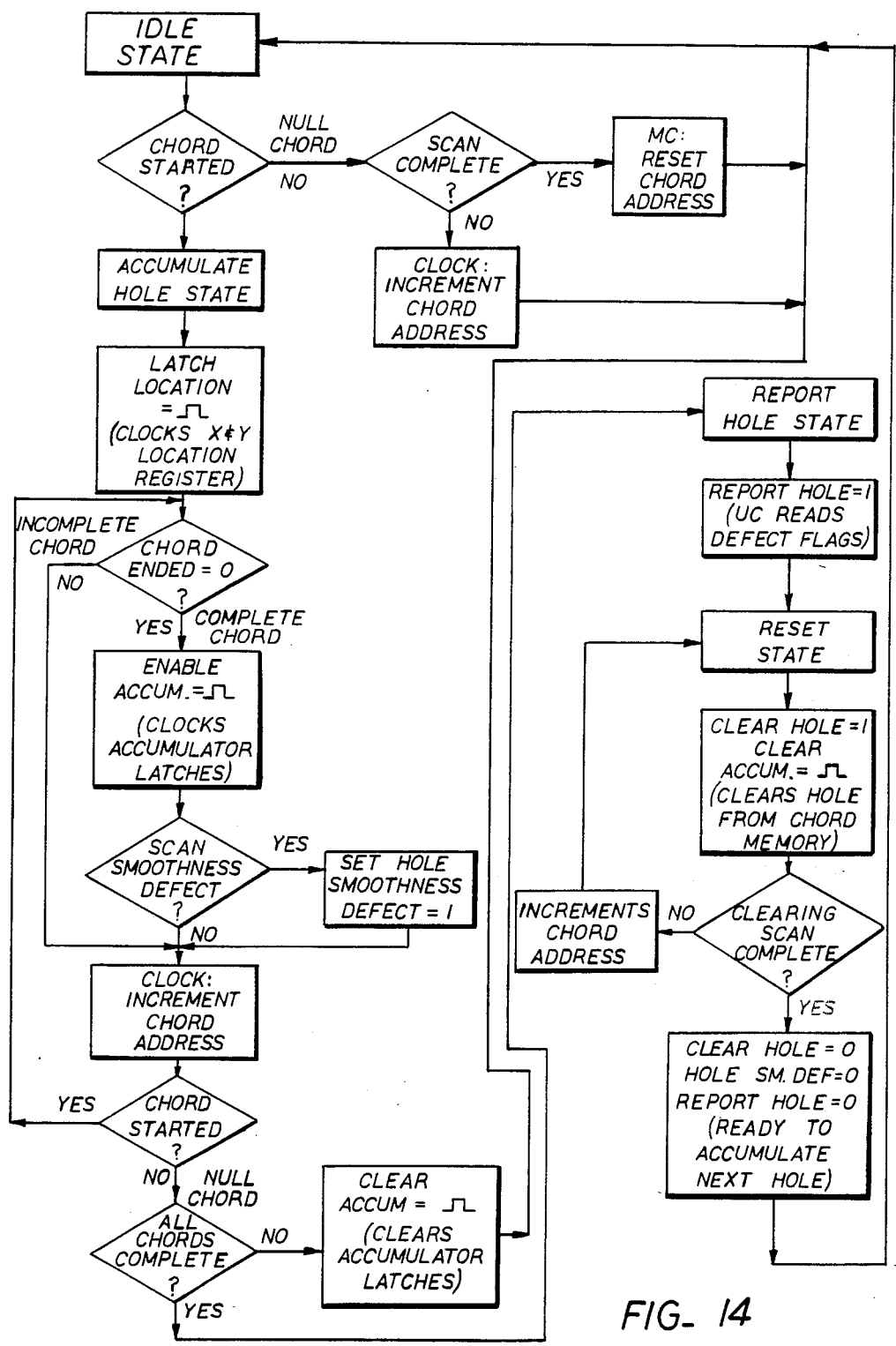
FIG. 14 is a flow diagram showing the logical steps used by the instruction control unit of FIG. 13.

FIGS. 13 and 14 respectively, show the circuit and the logic of the instruction memory 250 which, in conjunction with the chord status memory circuit 242, defines the state of the defect analyzer. Program instructions are stored in a state PROM (programmable read only memory) 328 and an instruction PROM 330. A state latch 332 provides feedback to the state PROM according to previously determined states. State latch 332 also provides a point of entry for scan and input ready signals from the microcomputer 216. Based upon previous instructions and the flags in the chord memory 308 at the current chord address, the state PROM 328 determines whether the defect analyzer circuit is in the idle, accumulate, report, or reset states.

Based upon the state determined by the state PROM and the smoothness flag, the instruction PROM 330 generates instruction signals that are latched by an instruction latch 334. When the accumulate state is first entered, a latch location signal 336 enables the (X,Y) locator circuit 248 to determine the Y coordinate of the lowermost chord for later determination of the Y coordinate of the hole center. Also while in the accumulate state, an enable accumulator signal 338 is generated to clock counters and latches in the diameter check and area check circuits 244 and 246.

After the hole has been completely inspected, as signified by a grouping of complete chords only, the state PROM 328 signifies a shift to the report state. A report hole signal 340 is generated by the instruction PROM to signal the microcomputer 216 that a hole inspection report is ready. A hole smoothness defect signal 342 indicates to the microcomputer whether any flags were set in the smoothness defect RAM 314 during hole accumulation. The diameter and area check circuits relay their results directly to the microcomputer bypassing the instruction memory.

After the hole inspection results are reported, the state PROM 328 shifts the state to reset. In the reset state, the instruction PROM 330 signals the chord status memory 242 via the clear hole signal 326 to clear the portion of the chord memory that corresponds to the hole just reported. At the same time, a clear accumulator signal 344 is generated to clear the counters and latches in the diameter check and area check circuits.

The logical steps that the instruction memory 250 uses in determining state are shown in FIG. 14. When in the idle state, the value of the chord started flag is examined, and if a null chord is indicated, the instruction memory waits for the next pixel cluster to be formed. By tracking the chord address, the microcomputer 216 determines whether the next cluster should be the next adjacent one on the same scan or, if at the end of a scan, the first cluster of the next scan.

When a started chord is found, the state shifts to accumulate, and a pulse is sent over the latch location signal 336. The defect analyzer 56 remains in the accumulate state until a null chord is found. While in the accumulate state, the enable accumulator signal 338 is clocked for each incomplete chord. If any of the flags in the smoothness defect RAM 314 are set, the hole smoothness defect flag 342 is set. When a null chord is finally found, the state returns to idle unless all of the chords just examined are complete which causes a state shift to the report hole state.

In the report hole state, the report hole signal 340 informs the microcomputer 216 that the inspection of a hole is complete. Next, the defect analyzer 56 enters the reset state to prepare to inspect the next hole. To accomplish this, the clear hole signal instructs the chord status memory circuit 242 to clear the appropriate portions of the chord memory 308, and the clear accumulator signal instructs the diameter check circuit 244 and the area check circuit 246 to clear their latches and registers. With that accomplished, the state PROM 328 shifts the state to idle to await another new or partially accumulated hole.

Hole area is calculated and tested against predetermined limits by the area check circuit 246, as shown in FIG. 15. The hole area is calculated by adding the chord lengths for all of the chords corresponding to the hole. This is accomplished by an adder 348 which adds the currently addressed chord length to the previously calculated subtotal stored in latch 350. The hole area is compared to limits by a window comparator. As in the smoothness checker 240, the minimum area is loaded into a latch 352 from the tolerance data bus 256 when clocked by a write minimum area signal 354. The area range is loaded in a latch 356 from data bus 256 when clocked by a write area range signal 358. A subtractor 360 subtracts the minimum area from the calculated area and inputs the difference to a comparator 362. If this difference is greater than the range value in latch 356, the comparator 362 outputs a logic high value on an area defect signal 364; otherwise a logic low value is output. The area defect signal communicates to the microcomputer 216 whether the hole passed or failed the objective area inspection.

The diameter check circuit 244 finds the hole diameter in both X and Y directions and compares those values to predetermined limits. The hole diameter in X is determined by finding the longest chord. Chord length is input into a latch 366 and a comparator 368. During each step in the accumulate state, the comparator determines whether the current chord length or the stored chord length is longer. If the current chord length is larger, the output of comparator 368, combined with the enable accumulator signal 338 by an AND gate 370, act to clock the current chord length into the latch 366. The X diameter thus found is compared to predetermined limits in another window comparator circuit. The minimum limit on the diameter in the X direction is latched into latch 372 and the range is latched into latch 374. Subtractor 376 and comparator 378 cooperate to indicate an X diameter defect, if present, to the microcomputer via an X diameter defect signal 380.

Hole diameter is computed in the Y direction by counting the number of completed chords in the chord memory using a counter 382. Again, the measured diameter is compared to predetermined limits using a window comparator circuit. The minimum limit on the diameter in the Y direction is latched into latch 384 and the range is latched into latch 386. Subtractor 388 and comparator 389 cooperate to indicate a Y diameter defect, if present, to the microcomputer via a Y diameter defect signal 392. Both the measured X diameter and the measured Y diameter are input via signals 394 and 396 to the (X,Y) locator circuit 248 for determination of the coordinate location of the hole.

Figure 17:
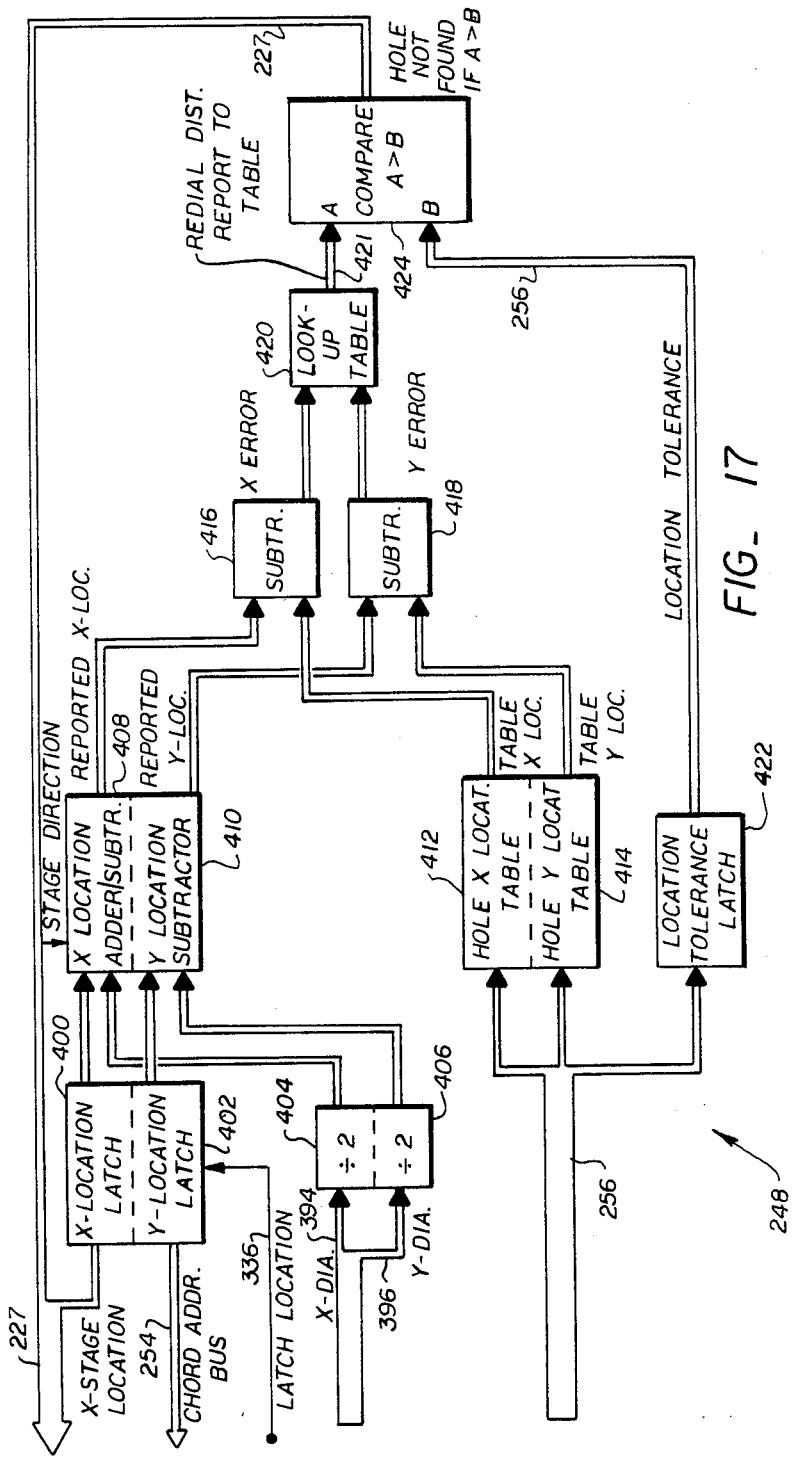
FIG. 17 is a block diagram illustrating the functional components of the X-Y Locator circuit shown in FIG. 9.

Referring now to FIG. 17 of the drawing, the XY locator 248 is shown to include an X-location latch 400, a Y-location latch 402 a pair of divide by two circuits 404 and 406, an X-location adder/subtractor circuit 408, a Y-location subtractor circuit 410, a hole X-location table 412, a hole Y-location table 414, a pair of subtractor circuits 416 and 418, a look up table 420, a location tolerance latch 422, and a comparitor 424. X-location latch 400 receives an X stage location signal from the input/output buffer 226 (FIG. 9) over the bus 227, while Y-location latch 402 receives an input from the chord counter 252 (FIG. 9) over bus 254.

Since the center position of a hole cannot know until both the horizontal and vertical sides thereof have been detected, as soon as the state machine of memory 250 (FIGS. 9 and 13) begins accumulating a hole it generates a signal on line 336 which is input to and latches the starting X- and Y-locations in latches 400 and 402 respectively, the X diameter and the Y diameter determined by unit 244 (FIG. 16) are then divided by units 404 and 406 and input to the adder/subtractor 408 and subtractor 410 respectively, where they are either added to or subtracted from the starting X and Y coordinates to determine the X and Y center coordinates which will be reported on lines 409 and 411. At the same time, the X location table 412 and Y-location table 414 are caused to generate X and Y coordinates which along with the reported X and Y locations are input to subtractors 416 and 418 which in turn generate X errors and Y errors which are feed into a look up table 420. Table 420 then generates a radial distance report which is input to the A terminal of comparator 424. At the same time, a tolerance signal stored in location tolerance latch 422 is input on line 256 to the B input of comparator 424. The location tolerance is then compared to the radial distance input, and so long as the radial distance is less than the input tolerance, the hole will be considered as having been found. However, if the radial distance is greater than the tolerance, the comparitor 424 will generate a signal on line 227 indicating that the hole has not been found and such signal will be transmitted back to the input output buffer 226 (FIG. 9) via bus 227. This operation will of course be repeated each time a hole is encountered.

Although the present invention has been described above in terms of a preferred embodiment specifically designed to test metal deposition masks, it will be understood that the system on various parts thereof could be adapted for other applications. For example, solid round objects instead of masks with round holes could be inspected with the present invention. Accordingly, it is Applicants' intent that the appended claims be interpreted as covering all such alterations, modifications or other applications as fall within the true spirit and scope of the invention.

What is claimed is:

1. A method for inspecting the perimeter smoothness of a nominally round opening in an object comprising the steps of:

forming a two dimensional representation of the opening, said representation including two dimensional array of uniformly spaced pixels of a size substantially smaller than the size of said opening with each pixel having a range of digital values which indicate the presence, partial presence, or absence of said opening at the spatial position represented by that pixel, said array of pixels representing said opening as a connected group of pixels having first values at one end of said range surrounded by pixels having second values at the other end of the range, with the boundary therebetween representing the perimeter of said opening; and examining the values of the pixels in one or more clusters surrounding said opening, each said cluster being composed of a group of several adjacent pixels arranged in a pattern with its center at said boundary, and determining that said perimeter is smooth at the location of a particular cluster if the number of pixels within said cluster having said first value is close to the number of pixels within said cluster having said second value, and wherein said perimeter is not smooth at said location if the number of pixels within said cluster having said first value is greatly disproportionate to the number of pixels within said cluster having said second value.

2. A method as recited in claim 1 for additionally inspecting the area of the opening in said object and further comprising the steps of:

counting the number of pixels in said array having said first value, said number being equal to an area count; and setting an area error flag if said area count is less than a predetermined minimum value representing the smallest permissible area, or if said area count is greater than a predetermined maximum value representing the largest permissible area.

3. A method as recited in claim 1 for additionally inspecting the diameter of the opening in said object and further comprising the steps of:

counting the number of pixels in said array having said first value and spanning the distance from a first edge of said representation of said opening to a second edge thereof along one dimension to find a first measured diameter;

counting the number of pixels in said array having said first value and spanning the distance from a third edge of said representation of said opening to a fourth edge thereof along another dimension to find a second measured diameter; and setting a diameter error flag if either said first measured diameter or said second measured diameter is less than a predetermined minimum value representing the smallest permissible diameter, or if either said measured diameter is greater than a predetermined maximum value representing the largest permissible diameter.

4. A method as recited in claim 1 wherein the axes of said two dimensional array are mutually perpendicular, said pixels are rectangular in shape, and said cluster is symmetrical about both axes.

5. A method as recited in claim 4 wherein said step of forming a two-dimensional representation of said object includes the steps of:

projecting an image of a portion of said object onto a one-dimensional column of uniformly spaced sensors, each said sensor being operable to detect the presence or absence of said image and to signal the presence of said image by generating a signal having a digital value of 1 and the absence of said image by generating a signal having a digital value of 0;

recording said signals in one column of a two-dimensional memory array;

moving said object in a direction perpendicular to the column length of said sensors to project an adjacent portion of said object onto said sensors;

recording the signals corresponding to said adjacent portion of said object in an adjacent column of said memory array;

repeating the previous two steps of moving said object and recording the signals for each adjacent portion of said object until at least a representation of a portion of said opening is contained in said memory array.

6. A method as recited in claim 5 wherein said object is moved a predetermined distance during each said moving step.

7. A method as recited in claim 5 wherein said object is moved at a constant velocity during said recording step.

8. A method as recited in claim 5 wherein said step of projecting an image of a portion of said object is accomplished by an optical lens mechanism, and wherein said sensors are photodiodes responsive to the intensity of light incident thereupon.

9. A method as recited in claim 8 wherein said object is opaque and is illuminated from the side opposite said sensors such that the illumination passes through said opening to said sensors.

10. A method as recited in claim 8 wherein said opening is a round aperture in an otherwise solid article and said object is illuminated from the side opposite said sensors.

11. A method as recited in claim 4 wherein said cluster of pixels includes a group of four pixels at the center thereof in a two-by-two square pattern, and wherein said cluster is determined to be positioned at said perimeter when two of the said four center pixels have values of 1 and the other two said center pixels have values of 0.

12. A method as recited in claim 11 wherein said cluster of pixels is an eight-by-eight symmetrical array with three pixels truncated at each corner thereof to form adjacent rows of four, six, eight, eight, eight, six, and four pixels, respectively.

13. A method as recited in claim 3 for additionally detecting the complete blockage of said opening or the presence of an unintended opening, further comprising the steps of:

determining the coordinates of the center of said opening relative to a datum point;

comparing said coordinates to a predetermined set of reference coordinates; and determining that said opening is blocked if no opening is encountered having coordinates within said predetermined tolerance of said reference coordinates; and determining that said opening is misintended if said coordinates do not fall within a predetermined tolerance of said reference coordinates.

14. A method of inspecting one or more round openings in an object wherein each said opening is of the same nominal size, said method comprising the steps of:

forming a two dimensional representation of at least a portion of the object, said representation including a two-dimensional array of rows and columns of uniformly spaced apart pixels of a size substantially smaller than said openings with each pixel having a first digital value to indicate the presence of an opening at the spatial position of that pixel, or a second digital value to indicate the absence of an opening thereat, said array of pixels representing each opening as a connected group of pixels having said first value surrounded by pixels having said second value, with the boundary therebetween representing the perimeter of said opening;

storing said representation in a pixel memory;

scanning said pixel memory by accessing clusters of pixels therein one cluster at a time and summing the values of the pixels in each cluster as that cluster is accessed, said scanning step beginning at one corner of said array of pixels and proceeding to advance in the direction of the rows of pixels, each said cluster being composed of portions of several adjacent rows and columns of pixels arranged in a symmetrical pattern;

setting a smoothness defect flag in a chord memory array whenever an accessed cluster is positioned such that the center of said cluster is located at a boundary of one of said openings and the number of pixels within said cluster having said first value is a predetermined relationship to the number of pixels within said cluster having said second value; and reporting a smoothness defect for an opening if any smoothness defect flags are set for that opening.

15. A method as recited in claim 14 additionally comprising the steps of:

setting a start chord flag in said chord memory array at a column corresponding to the position of an accessed cluster whenever the center of said cluster is positioned at said boundary and said start chord flag has not been previously set for said column;

incrementing a chord length register in said chord memory array at a column corresponding to the position of an accessed cluster whenever the center of said cluster is positioned inside the boundary of one of said objects;

setting an end chord flag in said chord memory array at a column corresponding to the position of an accessed cluster whenever the center of said cluster is positioned at said boundary and said start chord flag has been previously set for said column, said start chord flag and said end chord flag respectively designating the first and last pixels in a row of pixels that lies entirely within the boundaries of said representation of said object;

reporting an area defect for an opening if the sum of all of the chord length registers corresponding to that opening is less than a predetermined minimum area value or is greater than a predetermined maximum area value; and reporting a diameter defect for an opening of either the largest value in said chord length register corresponding to that opening or the number of non-second value columns in said chord length register corresponding to that opening is less than a predetermined minimum diameter value or is greater than a predetermined maximum diameter value.

16. A method as recited in claim 15 wherein the axes of said two dimensional array are mutually perpendicular, said pixels are rectangular in shape, and said cluster is symmetrical about both axes.

17. A method as recited in claim 15 wherein said step of forming a two-dimensional representation of said openings includes the steps of:

projecting an image of a portion of said object onto a one-dimensional array of uniformly spaced sensors, each said sensor being operable to detect the presence or absence of said image and to generate a signal indicating the presence of said image at the sensor by a digital value of 1 and the absence of said image at the sensor by a digital value of 0;

recording the first group of signals generated by said sensors into one column of said pixel memory, each sensor defining a separate row in said pixel memory;

moving said object in a direction perpendicular to said sensors to project an adjacent portion of said objects onto said arrays of sensors;

recording the second group of sensor signals corresponding to said adjacent portion of said object into an adjacent column of said pixel memory;

repeating the previous two steps of moving said object and recording the subsequent groups of sensor signals for each adjacent portion of said object until a complete representation of said openings is contained in said pixel memory.

18. A method as recited in claim 17 wherein said forming and said scanning steps are performed concurrently by accessing one of said clusters after each said group of signals is recorded, said cluster including a present sub-column of pixels corresponding to the present position of said sensor, and trailing pixels previously recorded in the same rows as said present pixels.

19. A method as recited in claim 17 wherein said object is moved a discrete distance during said moving step and is stationary during said recording step.

20. A method as recited in claim 17 wherein said object is moved at a constant velocity during said recording step.

21. A method as recited in claim 17 wherein said step of projecting an image of a portion of said object is accomplished by an optical lens mechanism, and wherein said sensors are photodiodes responsive to the intensity of light incident thereupon.

22. A method as recited in claim 21 wherein said object is opaque and is illuminated from the side opposite said sensors such that the illumination passes through said openings to said sensors.

23. A method as recited in claim 21 wherein said openings are perforations in an otherwise solid article and said object is illuminated from the side opposite said sensors.

24. A method as recited in claim 16 wherein said cluster of pixels has a group of four pixels at the center thereof in a square pattern of two-by-two, and wherein said cluster is positioned at said boundary when two of the four center pixels have said first value and the other two center pixels have said second value.

25. A method as recited in claim 15 for additionally detecting the misposition of an opening and further comprising the steps of:
    determining the coordinates of the center of said opening relative to a datum point;
    comparing said coordinates to a predetermined set of reference coordinates; and
    determining that said opening is mispositioned if said coordinates do not fall within a predetermined tolerance of said reference coordinates.

26. A method as recited in claim 16 for additionally detecting the blockage of an opening by determining that no set of coordinates falls within a predetermined tolerance of a set of reference coordinates corresponding to the intended location of an opening.

27. Inspection apparatus for inspecting the area, diameter, and surface smoothness of nominally round openings in an object comprising:
    carriage means for supporting the object to be inspected and for simultaneously moving such object along an inspection path;
    illumination means for illuminating portions of said object as it is moved along said path;
    optical means for focusing an image of said object at a focal plane;
    photosensitive detector means disposed at said focal plane at right angles to said inspection path for generating sensor signals corresponding to said image of said object incident thereon;
    signal processing means for processing said sensor signals to inspect said openings, said signal processing means including memory means for storing said sensor signals, smoothness checking means for constructing a digital representation of portions of said object from said sensor signals and for measuring the radius of curvature of said openings, and for comparing said measured radius of curvature to an inspection standard, diameter checking means for measuring the diameters of said openings from said digital representation and for comparing said measured diameters to an inspection standard, area checking means for measuring the area of said openings from said digital representation and for comparing said measured areas to an inspection standard.

28. Inspection apparatus as recited in claim 27 and further including opening presence checking means for determining that an opening is not present if no opening is found to lie within a predetermined tolerance of an intended opening location.

* * * * *